US010258516B2

(12) United States Patent
Day et al.

(10) Patent No.: US 10,258,516 B2
(45) Date of Patent: Apr. 16, 2019

(54) TREATED THREE-DIMENSIONAL APERTURED LINERS

(71) Applicant: Kimberly-Clark Worldwide, Inc., Neenah, WI (US)

(72) Inventors: Virginia Lee Day, Woodstock, GA (US); Frank Paul Abuto, Duluth, GA (US); Sridhar Ranganathan, Suwanee, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 123 days.

(21) Appl. No.: 13/955,148

(22) Filed: Jul. 31, 2013

(65) Prior Publication Data

US 2015/0038933 A1 Feb. 5, 2015

(51) Int. Cl.
*A61F 13/512* (2006.01)
*A61F 13/513* (2006.01)
(Continued)

(52) U.S. Cl.
CPC ...... *A61F 13/512* (2013.01); *A61F 13/51113* (2013.01); *A61F 13/52* (2013.01);
(Continued)

(58) Field of Classification Search
CPC .............. A61F 13/512; A61F 13/52; A61F 2013/51366; A61F 13/51104;
(Continued)

(56) References Cited

U.S. PATENT DOCUMENTS

| 2,069,092 A | 1/1937 | Jackson, Jr. | |
| 3,462,294 A * | 8/1969 | Thomas | 442/80 |

(Continued)

FOREIGN PATENT DOCUMENTS

| EP | 1075388 B1 | 11/2002 |
| EP | 1059908 B1 | 10/2004 |

(Continued)

OTHER PUBLICATIONS

Co-pending U.S. Appl. No. 13/955,392, filed Jul. 31, 2013, by Day et al. for "Treated Three-Dimensional Apertured Surge."

*Primary Examiner* — Peter S Vasat
(74) *Attorney, Agent, or Firm* — Kimberly-Clark Worldwide, Inc.

(57) ABSTRACT

A bodyside liner material for use in disposable absorbent personal care products has an average material plane and includes a plurality of raised areas extending in a z-direction from the average material plane; a plurality of apertures through the liner material; a hydrophobic treatment agent disposed on the raised areas; and a plurality of land areas disposed between the raised areas, wherein the land areas are hydrophilic. The bodyside liner material can also include a plurality of raised areas extending in a z-direction from the average material plane; a plurality of depressed areas alternating with the plurality of raised areas, wherein the depressed areas extend in the opposite z-direction from the average material plane, and wherein the depressed areas are hydrophilic; a plurality of apertures through the liner material, wherein the apertures are disposed only in the depressions; and a hydrophobic treatment agent disposed on the raised areas.

12 Claims, 6 Drawing Sheets

(51) Int. Cl.
  *A61F 13/51* (2006.01)
  *A61L 15/48* (2006.01)
  *A61F 13/511* (2006.01)
  *A61L 15/42* (2006.01)

(52) U.S. Cl.
  CPC .............. *A61L 15/42* (2013.01); *A61L 15/48* (2013.01); *A61F 2013/51366* (2013.01); *Y10T 428/24273* (2015.01)

(58) Field of Classification Search
  CPC ............ A61F 13/5126; A61F 13/51305; A61F 13/537; A61F 2013/53778; A61F 2013/53782
  USPC ................................ 604/380, 381, 382, 383
  See application file for complete search history.

(56) References Cited

U.S. PATENT DOCUMENTS

| | | | |
|---|---|---|---|
| 3,881,987 | A | 5/1975 | Benz |
| 4,681,577 | A | 7/1987 | Stern et al. |
| 5,414,914 | A * | 5/1995 | Suzuki et al. ................. 28/105 |
| 5,439,458 | A | 8/1995 | Noel et al. |
| H1511 | H | 12/1995 | Chappell et al. |
| 5,624,422 | A | 4/1997 | Allen |
| 5,647,862 | A | 7/1997 | Osborn, III et al. |
| 5,658,639 | A | 8/1997 | Curro et al. |
| 5,879,343 | A | 3/1999 | Dodge, II et al. |
| 5,906,879 | A | 5/1999 | Huntoon et al. |
| 5,990,377 | A | 11/1999 | Chen et al. |
| 6,025,049 | A | 2/2000 | Ouellette et al. |
| 6,190,369 | B1 | 2/2001 | Palumbo et al. |
| 6,410,823 | B1 | 6/2002 | Daley et al. |
| 6,458,111 | B1 | 10/2002 | Onishi et al. |
| 6,521,241 | B1 | 2/2003 | Minerath, III et al. |
| 6,692,603 | B1 | 2/2004 | Lindsay et al. |
| 6,786,894 | B2 | 9/2004 | Divo et al. |
| 7,718,243 | B2 | 5/2010 | Curro et al. |
| 8,030,536 | B2 | 10/2011 | Ponomarenko et al. |
| 8,034,990 | B2 | 10/2011 | Berland et al. |
| 2002/0099347 | A1 * | 7/2002 | Chen et al. .................... 604/369 |
| 2002/0103469 | A1 | 8/2002 | Chen et al. |
| 2002/0107495 | A1 | 8/2002 | Chen et al. |
| 2003/0171729 | A1 | 9/2003 | Kaun et al. |
| 2005/0096614 | A1 | 5/2005 | Perez et al. |
| 2005/0100713 | A1 | 5/2005 | Busam et al. |
| 2007/0255247 | A1 | 11/2007 | Moberg-Alehammar et al. |
| 2007/0298213 | A1 | 12/2007 | Noda et al. |
| 2008/0090050 | A1 | 4/2008 | Seyler et al. |
| 2008/0147024 | A1 * | 6/2008 | Potts et al. ..................... 604/358 |
| 2009/0137976 | A1 | 5/2009 | Suzuki |
| 2009/0233046 | A1 * | 9/2009 | Iulianetti ....................... 428/137 |
| 2010/0121298 | A1 | 5/2010 | Seyler et al. |
| 2010/0159195 | A1 * | 6/2010 | Quincy, III ............ B05D 5/083 428/141 |
| 2013/0158497 | A1 | 6/2013 | Yamaguchi et al. |

FOREIGN PATENT DOCUMENTS

| | | |
|---|---|---|
| EP | 1570824 A1 | 9/2005 |
| GB | 1263311 A | 2/1972 |
| JP | 09-299402 A | 11/1997 |
| WO | WO 1998/037846 A1 | 9/1998 |
| WO | WO 2007/035038 A1 | 3/2007 |

* cited by examiner

Fig. 7: BM Amount in Different Layers

Fig. 8: BM Staining

Fig. 11: BM Amount in Different Layers

Fig. 12: BM Staining

TREATED THREE-DIMENSIONAL APERTURED LINERS

BACKGROUND

The present disclosure relates to personal care products, particularly disposable absorbent articles including hydrophilically-treated apertures that help the surface of the article to appear and feel clean.

A number of disposable, personal care articles that collect body fluids exist; however, their tendency to leak off the surface before the liquid absorbent capacity is entirely used is an ongoing challenge that faces many manufacturers. Additionally, certain fluids, such as menses and runny BM (feces), have viscoelastic properties that make obtaining good intake and distribution performance particularly problematic. In particular, the relatively high viscosity and/or elasticity of such fluids tend to interfere with the absorption and distribution of the fluids within the absorbent article. In other instances, intake performance of an absorbent article can be impeded when components of the menses block the channels between the particles or fibers contained in the absorbent article. This phenomenon is often referred to as fouling. Although attempts have been made to improve the effects of fouling through modification of the viscoelastic properties of the fluid itself, actual improvement into the absorbent article still needs development.

In addition to problems with leakage in some disposable, personal care articles, there are also hygienic issues that directly affect the user. Often the body fluid sits in direct contact with the user that makes for an unpleasant and unclean feel. Particularly with feminine hygiene products such as sanitary napkins, the unpleasant or unclean feeling that can often be caused by bodyside liner stains can lead to poor perception in product performance and the inability to get maximum use from the product.

Therefore, there is a need in the art for personal care products, such as absorbent articles, that provides improved intake and distribution performance, reduced leakage, reduced stains, reduced surface rewet or flowback for an overall cleaner, drier and more pleasant feel, and user experience.

Contemporary diapers are not as effective as could be in the management of runny-BM from breast-fed newborn babies. BM tends to remain (pool) on the diaper liner surface with minimal amount transferred to and absorbed by the absorbent core. A high amount of pooled BM with a large stain-size on the diaper surface gives a negative indication and perception to the caregiver that the diaper is ineffective in handling BM. Besides the negative perception, BM on the liner is messy to clean and is clearly an unmet consumer need. It is therefore desirable to transfer as much BM to below the liner as possible.

SUMMARY

This disclosure utilizes novel 3-D materials with optimized apertures and with combinations of hydrophilic and hydrophobic treatments strategically applied to the materials to improve diaper BM absorption and transfer to below the liner. When most of the BM is absorbed, a smaller mess is left on the baby for the caregiver to clean and there is provided a cleaner-looking diaper surface. The 3-D structures and treatment combinations of the present disclosure are not limited to BM management and can be applied to improve absorption of other fluids including menses, urine and the like.

The present disclosure accomplishes this by presenting a bodyside liner material for use in disposable absorbent personal care products, the liner material having an average material plane and including a plurality of raised areas extending in a z-direction from the average material plane; a plurality of apertures through the liner material; a hydrophobic treatment agent disposed on the raised areas; and a plurality of land areas disposed between the raised areas, wherein the land areas are hydrophilic.

The present disclosure also accomplishes this by presenting a bodyside liner material for use in disposable absorbent personal care products, the liner material having an average material plane and including a plurality of raised areas extending in a z-direction from the average material plane; a plurality of depressed areas alternating with the plurality of raised areas, wherein the depressed areas extend in the opposite z-direction from the average material plane, and wherein the depressed areas are hydrophilic; a plurality of apertures through the liner material, wherein the apertures are disposed only in the depressions; and a hydrophobic treatment agent disposed on the raised areas.

Also presented is a personal care article including a nonwoven fluid permeable liner material having a body-facing surface and an opposing backside surface, a fluid impermeable backsheet and at least one intermediate layer disposed therebetween, wherein the fluid permeable liner material includes raised areas and apertures, wherein at least some of the raised areas are treated with a hydrophobic treatment agent, and wherein at least some of the apertures are treated with a hydrophilic treatment agent.

BRIEF DESCRIPTION OF THE DRAWINGS

The foregoing and other features and aspects of the present disclosure and the manner of attaining them will become more apparent, and the disclosure itself will be better understood by reference to the following description, appended claims and accompanying drawings, where:

Repeat use of reference characters in the present specification and drawings is intended to represent the same or analogous features or elements of the present disclosure. The drawings are representational and are not necessarily drawn to scale. Certain proportions thereof might be exaggerated, while others might be minimized.

DETAILED DESCRIPTION

While the specification concludes with the claims particularly pointing out and distinctly claiming the disclosure, it is believed that the present disclosure will be better understood from the following description.

All percentages, parts and ratios are based upon the total weight of the compositions of the present disclosure, unless otherwise specified. All such weights as they pertain to listed ingredients are based on the active level and, therefore, do not include solvents or by-products that can be included in commercially available materials, unless otherwise specified. The term "weight percent" can be denoted as "wt. %" herein. Except where specific examples of actual measured values are presented, numerical values referred to herein should be considered to be qualified by the word "about."

As used herein, the phrase "absorbent article" generally refers to devices that absorb and contain body fluids, and more specifically, refers to devices that are placed against or near the skin to absorb and contain the various fluids discharged from the body and, in particular, viscoelastic fluids. Examples of absorbent articles include, but are not limited to, absorbent articles intended for personal wear, such as diapers; incontinence products; feminine hygiene products, such as feminine napkins, panty liners, tampons, and interlabial pads; other personal garments; and the like.

As used herein, "fouling" means the change in permeability of a fluid as it passes through a porous medium. More particularly, fouling is the reduction in permeability that occurs when components of a fluid pass through a porous medium and interact with the material structure, decreasing the inherent permeability of the porous material.

The term "hydrophilic," as used herein, refers to surfaces with water contact angles well below 90°.

The term "hydrophobic," as used herein, refers to the property of a surface to repel water with a water contact angle from about 90° to about 130°.

As used herein, "rewetting" refers to the amount of fluid that comes from the absorbent core back into and through the top layer nonwoven surface. This can also be referred to as flowback.

The term "superhydrophobic" refers to the property of a surface to repel water very effectively. This property is quantified by a water contact angle generally exceeding 130°.

The present disclosure relates to improved personal care products, particularly disposable absorbent articles. Personal care products of the present disclosure include, but are not limited to, feminine hygiene products like sanitary wipes and menses absorbing devices (e.g., sanitary napkins and tampons), infant and child care products such as disposable diapers, absorbent underpants, and training pants, wound dressings such as bandages, incontinent products, products for wiping and absorbing oils, and the like.

Figure 1:
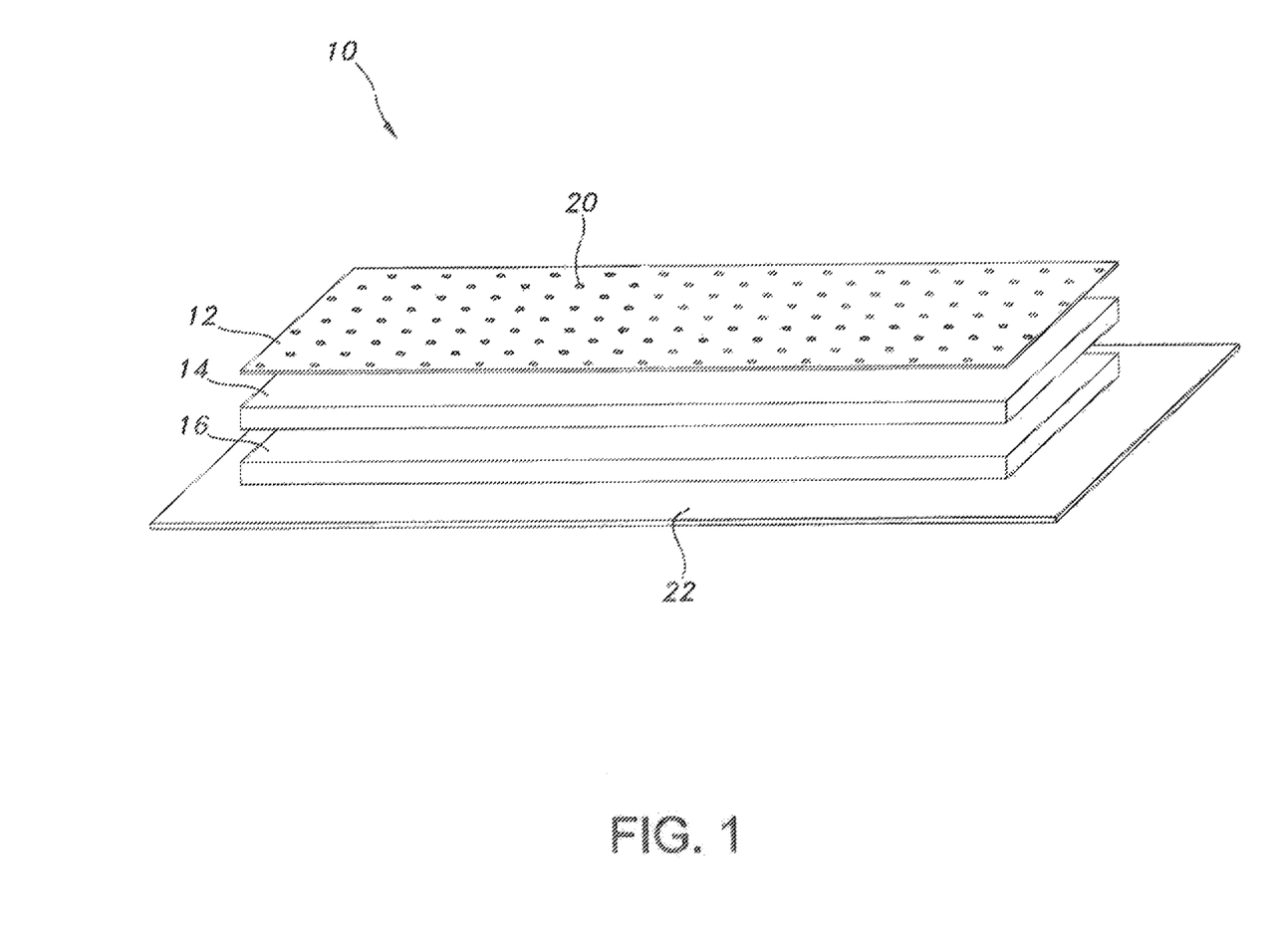
FIG. 1 is a schematic illustration of various layers of a personal care article of the present disclosure.

A portion of a disposable absorbent article 10 such as that illustrated in FIG. 1, for example, can include a liquid permeable topsheet or liner 12, a substantially liquid impermeable backsheet 22 joined to the liner material 12, and an absorbent core 16 positioned and held between the liner material 12 and the backsheet 22. The liner material 12 is operatively permeable to the liquids that are intended to be held or stored by the absorbent article 10, and the backsheet 22 can be substantially impermeable or otherwise operatively impermeable to the intended liquids. The absorbent article 10 can also include an additional layer(s) 14 such as that shown in FIG. 1. This additional layer(s) 14 can be a liquid intake layer, a surge layer, a liquid wicking layer, a liquid distribution layer, a transfer layer, a barrier layer, and the like, as well as multiples and combinations thereof.

Disposable absorbent articles 10 and the components thereof can operate to provide a body-facing surface (top surface of the liner material 12) and a garment-facing surface (back surface of the backsheet 22). As used herein, the "body-facing" or "bodyside" surface refers to the surface of the liner material 12 that is disposed toward or placed adjacent to the body of the wearer during ordinary use. The "garment-side surface" refers to the backsheet 22 where the back surface is disposed away from the wearer's body and adjacent to the garment of the wearer during ordinary use. Suitable absorbent articles are described in more detail in U.S. Pat. No. 7,632,258.

The fluid permeable liner material 12 of the present disclosure can be left untreated or can be treated with a hydrophobic or superhydrophobic composition that helps to keep fluids from sitting atop the surface that can leave an unpleasant and/or unclean feeling from stains, accumulated debris, or wetness on the surface. The liner material 12 is typically provided with apertures, slits, and the like to ensure fluid permeability when the liner material 12 is treated with hydrophobic or superhydrophobic compositions. The disposable absorbent article 10 of the present disclosure is particularly adapted to receive fluids having viscoelastic properties, such as menses, mucous, blood products, and feces, among others to reduce stain area, reduce rewet, improve fluid intake, distribution, absorption properties and decrease leakage. More importantly, the fluid permeable liner material 12 is preferably a substantially hydrophobic nonwoven such as spunbond, spunbond-meltblown-spunbond (SMS), Bonded Carded Web (BCW), spunlace, or coform. The fluid permeable liner material 12 can include a three-dimensional profile and/or apertures 20. The apertures 20 can be treated with a hydrophilic treatment agent, the treatment agent increasing the surface energy in and around the apertures to preferentially channel fluid flow into the apertures 20 to provide advantages of the present disclosure in protecting against stains, re-wetting, particulate debris accumulation on the body-facing surface and other unpleasantries.

Although the present disclosure is discussed primarily in reference to BM absorption in disposable absorbent articles such as diapers, it will be readily apparent to one skilled in the art based on the disclosure that the products and methods described herein can also be used in combination with numerous other absorbent articles designed to absorb fluids other than BM such as menses, urine, and the like.

This disclosure utilizes novel 3-D materials with optimized apertures and combinations of hydrophilic and hydrophobic treatments strategically applied to the materials to improve diaper BM absorption and transfer. When most of the runny BM is absorbed, a smaller mess is left on the baby for the caregiver to clean and a cleaner-looking diaper surface is provided. The 3-D structures and treatment combinations of the present disclosure are not limited to BM management and can be applied to improve absorption of other fluids including menses, urine and the like. The improvement in performance is generally measured by assessing BM pooling, stain size, and the amount of BM in different layers (liner, surge, core).

3-D structures can include bumps, pockets, raised areas, depressed areas, corrugations, and channels. Apertures are typically disposed in the depressed areas or valleys between the bumps/corrugations/channels. In other aspects, the apertures can be distributed uniformly or non-uniformly regardless of bump or valley. In general, the hydrophilic treatment agent is patterned such that it is disposed in the valleys, and the hydrophobic treatment agent is patterned such that it is disposed on the bumps or the raised portions of the topographical surface. Topsheet or liner materials tested include textured 3-D coform, corrugated paper, airlaid material, and 3-D nonwoven from Textor Technologies Pty Ltd, 41 Tullamarine Park Road, VIC 3043, Melbourne, Australia.

It was demonstrated that a 3-D-structured liner with apertures and such patterned treatments transferred more BM to the core, exhibited slightly smaller stain size, and showed reduced BM pooling.

Fluid Permeable Liner Material

The absorbent article 10 of the present disclosure includes a fluid permeable liner material 12 that is preferably a nonwoven, body-facing fibrous sheet material. The present disclosure provides an advantage over liner materials including a thermoplastic film because nonwovens are generally softer, cause less sweating and irritation from sweat, and avoids the plastic feel or rustling that is often associated with plastics and films. Nonwovens of the present disclosure include, but are not limited to, spunbond, meltblown, coform, air-laid, bonded-carded web materials, hydroentangled (spunlace) materials, combinations thereof and the like. For example, the fibers from which the nonwoven material is made can be produced by meltblowing or spunbonding processes, including those producing bicomponent, biconstituent, or polymer blend fibers that are well known in the art. These processes generally use an extruder to supply melted thermoplastic polymer to a spinneret where the polymer is fiberized to yield fibers that can be staple length or longer. The fibers are then drawn, usually pneumatically, and deposited on a moving formation mat or belt to form the nonwoven fabric. The fibers produced in the spunbond and meltblown processes can be microfibers. Microfibers of the present disclosure are small diameter fibers having an average diameter not greater than about 75 microns, for example, having an average diameter of from about 0.5 microns to about 50 microns, or more particularly, microfibers having an average diameter of from about 2 microns to about 40 microns.

Spunbond nonwoven fabrics are generally bonded in some manner as they are produced to give them sufficient structural integrity to withstand the rigors of further processing into a finished product. Bonding can be accomplished in a number of ways including hydroentanglement, needling, ultrasonic bonding, adhesive bonding, stitchbonding, through-air bonding, and thermal bonding.

The nonwoven also can be a bonded carded web. Bonded carded webs are made from staple fibers that are usually purchased in bales. The bales are placed in a picker that separates the fibers. Then, the fibers are sent through a combing or carding unit that further breaks apart and aligns the staple fibers in the machine direction to form a generally machine direction-oriented fibrous nonwoven web. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding devices are used to bond the fibers together, usually in a localized bond pattern, though the web can be bonded across its entire surface if so desired. Another suitable bonding method, particularly when using bicomponent staple fibers, is through-air bonding.

The nonwoven can also be produced through airlaying. The production of airlaid nonwovens is well defined in the literature and documented in the art. Examples include the DanWeb process as described in U.S. Pat. No. 4,640,810 to Laursen et al., the Kroyer process as described in U.S. Pat. No. 4,494,278 to Kroyer et al., the processes described in U.S. Pat. No. 5,527,171 to Soerensen, the method of U.S. Pat. No. 4,375,448 to Appel et al., and other similar methods.

The nonwoven of the present disclosure can also be a multilayer laminate. An example of a multilayer laminate is an aspect wherein some of the layers are spunbond and some meltblown such as a spunbond/meltblown/spunbond (SMS) laminate as disclosed in U.S. Pat. No. 4,041,203 to Brock et al., U.S. Pat. No. 5,169,706 to Collier, et al, and U.S. Pat. No. 4,374,888 to Bornslaeger. Such a laminate can be made by sequentially depositing onto a moving forming belt, first a spunbond fabric layer, then a meltblown fabric layer, and last another spunbond layer, and then bonding the laminate in a manner described below. Alternatively, the fabric layers can be made individually, collected in rolls, and combined in a separate bonding step. Such fabrics usually have a basis weight of about 0.1 to 12 OSY (ounces per square yard) (6 to 400 gsm), or more particularly from about 0.75 to about 3 OSY.

The 3-D materials of the present disclosure are nonwovens with different 3-D topography exemplified by bumps, channels, corrugations, grooves, valleys, dots, and the like of varying heights, dimensions, and spacing. For example, and in various aspects of the present disclosure, the liner material can be arranged and manufactured as described as the body-facing material in U.S. patent application Ser. No. 13/665,812, which is incorporated herein to the extent it does not conflict herewith.

Figure 2:
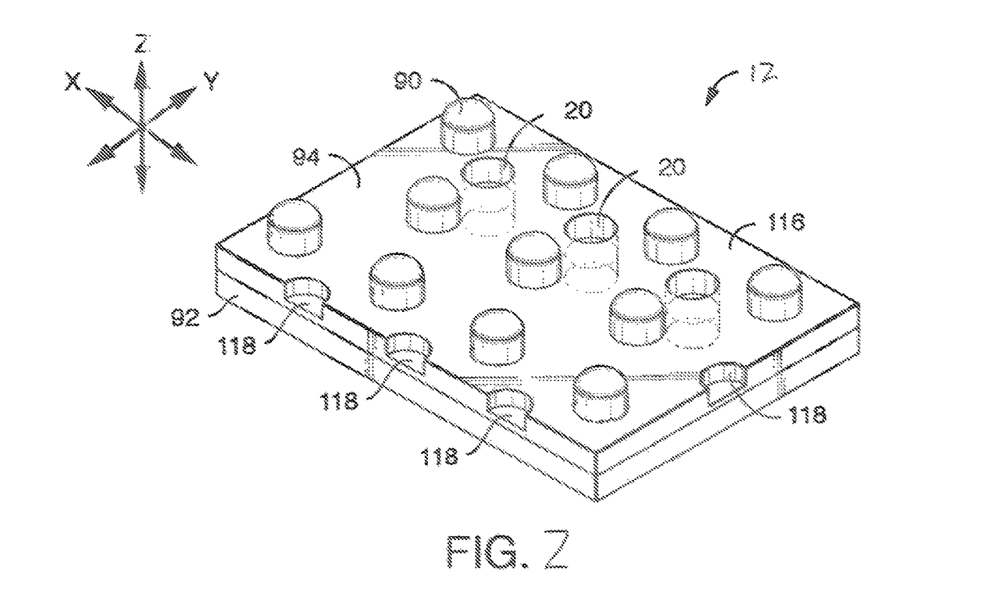
FIG. 2 illustrates a perspective schematic view of a portion of the liner material of FIG. 1.

As illustrated in FIG. 2, a liner material or topsheet 12 can be a fluid entangled laminate web with projections 90 extending outwardly and away from at least one intended external surface of the laminate web. In one aspect, the projections 90 can be hollow. The liner material 12 can have two or more layers such as an optional support layer 92 and a projection layer 94.

In one aspect, the projections 90 can be filled with fibers from the projection layer 94 and/or the optional support layer 92. In another aspect, the projections 90 can be hollow. The projections 90 can have closed ends that can be devoid of apertures. In some aspects, however, it can be desirable to increase the pressure and/or dwell time of the impinging fluid jets in the entangling process as described herein to create one or more apertures (not shown) in each of the projections 90. Apertures can also be formed into the body facing material via forming posts (not shown). Such apertures can be formed in the closed ends and/or side walls of the projections 90. Such apertures are to be distinguished from interstitial fiber-to-fiber spacing, which is the spacing from one individual fiber to the next individual fiber.

In various aspects, the projections 90 can be round when viewed from above with somewhat domed or curved tops or closed ends, such as seen when viewed in a cross-section. The actual shape of the projections 90 can be varied depending on the shape of the forming surface into which the fibers from the projection layer 94 are forced. Thus, while not limiting the variations, the shapes of the projections 90 can be, for example, round, oval, square, rectangular, triangular, diamond-shaped, etc. Both the width and height of the projections 90 can be varied as can be the spacing and pattern of the projections 90. In one aspect, various shapes, sizes and spacing of the projections 90 can be utilized in the same projection layer 94.

The projections 90 can be surrounded by land areas 116. The land areas 116 can be relatively flat and planar, as shown in FIG. 2, or topographical variability can be built into the land areas 116. For example, in one aspect, a land area 116 can have a plurality of three-dimensional shapes formed into it by forming the projection layer 94 on a three-dimensionally-shaped forming surface such as is disclosed in U.S. Pat. No. 4,741,941 to Engelbert et al. assigned to Kimberly-Clark Worldwide and incorporated herein by reference to the extent it does not conflict herewith. For example, in one aspect, a land area 116 can be provided with depressed areas 118 that can extend all or part way into the projection layer 94 and/or the support layer 92. In addition, a land area 116 can be subjected to embossing, which can impart surface texture and other functional attributes to the land area 116. In another aspect, a land area 116 and the liner material 12 as a whole can be provided with apertures 20 that can extend through the liner material 12 so as to further facilitate the movement of fluids (such as the liquids and solids that make up body exudates) into and through the liner material 12. Such apertures 20 are to be distinguished from interstitial fiber-to-fiber spacing, which is the spacing from one individual fiber to the next individual fiber.

The projections 90 of the liner material 12 can be provided in any orientation as deemed suitable. In one aspect, the projections 90 of the liner material 12 can be provided randomly to the liner material 12. In another aspect, the projections 90 can be oriented linearly in the x- and/or y-directions of the liner material 12. The land areas 116 of the liner material 12 can be provided in any orientation as deemed suitable. In one aspect, the land areas 116 can be oriented linearly in the x- and/or y-directions of the liner material 12.

In another aspect, the projections 90 can have varying heights, diameters, and concentrations in different areas of the liner material 12. In such an aspect, for example, the projections 90 can have a first height in one area of the liner material 12 and a different height in a different area of the liner material 12.

In other aspects, the projections 90 and/or the land areas 116 can be provided in a patterned orientation. Non-limiting examples of patterned orientations can include, but are not limited to, lines, circles, squares, rectangles, triangles, ovals, stars, and hexagons.

Hydrophobic/Superhydrophobic Coating

The nonwoven material of the present disclosure can be treated with a hydrophobic treatment agent, particularly one in the form of a hydrophobic or a superhydrophobic composition. If treated, a major portion of the surface of the nonwoven liner material 12 can be treated with a hydrophobic treatment agent selected from a hydrophobic composition, a superhydrophobic composition, or combinations thereof. The other portion of the surface will include hydrophilically-treated apertures 20 as will be subsequently detailed. In particularly preferred aspects, the projections 90 are treated with hydrophobic and/or superhydrophobic compositions or combinations thereof. It is possible to treat projections 90 in a section or area of the liner material 12 with a hydrophobic composition and a different area with superhydrophobic composition. The treatments can therefore be applied in any patterns and combinations of patterns without limitation. Similarly, land areas 116 can be treated with hydrophilic agents of various types such as various surfactants.

The hydrophobic treatment agent can be a hydrophobic polymer that is dispersible in water and including, but not limited to, fluorinated or perfluorinated polymers. The fluorinated or perfluorinated polymer can be modified by introducing a comonomer onto its molecular structure. Suitable comonomers include, but are not limited to, ethylenically-unsaturated monomers including functional groups that are capable of being ionized in water. One example is an ethylenically-unsaturated carboxylic acid, such as acrylic acid. One example of a hydrophobic composition is a commercially-available modified perfluorinated polymer compound available from DuPont as a water-based product under the trade name CAPSTONE ST-100.

In addition to the above examples, other hydrophobic materials suitable for the present disclosure are well defined and documented in the art. For example, U.S. Patent Publication No. 2002/0064639 describes hydrophobic compositions selected from the group consisting of silicones, fluorochemicals, zirconium compounds, oils, latexes, waxes, crosslinking resins, and blends thereof. Representative water repellent fluorochemical compounds described in U.S. Pat. No. 7,407,899 include fluorochemical urethanes, ureas, esters, ethers, alcohols, epoxides, allophanates, amides, amines (and salts thereof), acids (and salts thereof), carbodiimides, guanidines, oxazolidinones, isocyanurates, and biurets. U.S. Pat. No. 6,548,732 describes hydrophobic substances from the group consisting of theobroma oil, cacao butter, cocoa butter, petrolatum, mineral jelly, white mineral oil, dimethicone, zinc oxide preparation, chinese white, zinc white, beeswax, lanolin, jojoba oil, and combinations thereof. Additionally, U.S. patent application Ser. No. 13/193,065, filed Jul. 28, 2011, discusses substrates that exhibit superhydrophobic properties when treated with a composition including a hydrophobic component selected from fluorinated polymers, perfluorinated polymers, and mixtures thereof; nano-structured particles selected from fumed silica, hydrophobic titania, zinc oxide, nanoclay, and mixtures thereof; and water for an overall water-based, non-organic solvent. Examples of such compositions and surfaces in U.S. patent application Ser. No. 13/193,065 exemplify the superhydrophobic treated surfaces that can be used as the nonwoven liner material of the present disclosure.

The present disclosure presents both hydrophobic and superhydrophobic coated nonwovens to aid in reducing the presence of body fluids on the body-facing surface of the liner material 12, making it more likely for the body fluid to gravitate towards the hydrophilic apertures 20 and into the absorbent core 16.

Superhydrophobic-treated liner materials are those with water contact angles of 150° or greater that can be achieved, for example, by altering the topography of the surface such as through elevations and depressions to create a rough surface and then applying hydrophobic composition(s) thereto. U.S. Pat. No. 6,800,354, for example, describes a coating having a "nanoscale" structured surface such as by metal oxide particles with a suitable hydrophobic layer disposed on the structured substrate surface. Various other techniques for rendering surfaces superhydrophobic are also documented in, for example, U.S. Patent Publication No. 2009/0298369. These techniques include the use of roughening hydrophobic polymers such as fluorinated polymers, polydimethylsiloxane, paraffinic hydrocarbons, and the like via templating methods, electrospinning to yield small fiber diameters, controlling crystallization, and the like. Alternatively, a rough surface can be made by other techniques such as etching, lithography, sol-gel processing, layer-by-layer assembly, and the like and the surface modified with a low surface energy material like those hydrophobic materials mentioned previously. Another approach to achieve superhydrophobic properties is to coat a surface with a liquid dispersion that contains at least one low-surface energy component, such as a perfluorinated polymer, in combination with roughening features such as micro and nano structure forming particles that impart surface roughness when the coating composition is sprayed, padded, or applied through other common application techniques.

Apertured Liner Material

The nonwoven liner material 12 of the present disclosure includes treated and/or untreated apertures 20 for attracting body fluids from the body-facing surface into the absorbent core 16. The apertures 20 can be uniform in size or can be tapered or conical in shape, having a larger opening near the top and a smaller opening near the bottom. Larger opening geometric shapes can be, but are not limited to, circles, triangles, pentagons, ovals, symmetrical, non-symmetrical, and the like. The apertures 20 can also be patterned to show various designs or create advantaged depositions of the apertures in particular articles in order to minimize re-wetting and/or stains. At least a portion of the apertures 20 will be treated with a hydrophilic treatment agent. Thus, at least about 10%, at least about 25%, at least about 50%, at least about 75%, or 100% of the apertures within the nonwoven can include a hydrophilic treatment. The apertures can be treated and untreated in a pattern as a design for aesthetically pleasing visual cues, or for functional advantages to minimize re-wetting and/or staining in particular areas of the nonwoven, or for a combination of both aesthetic and functional features. Aperture diameters measured on the garment facing surface of the liner material can range from about 0.1 mm to about 5 mm, from about 0.4 mm to about 1.5 mm, or from about 0.5 mm to about 1.0 mm. The aperture density can also range from about $7.8 \times 10^3$ apertures/m$^2$ to about $1.9 \times 10^6$ apertures/m$^2$, from about $4.7 \times 10^4$ apertures/m$^2$ to about $9.3 \times 10^5$ apertures/m$^2$, or from about $1.6 \times 10^5$ apertures/m$^2$ to about $3.1 \times 10^5$ apertures/m$^2$. The apertures can extend through the thickness of the liner material 12 from the body-facing surface through and to the backside of the liner material 12. In some instances such as with a multi-layered laminate liner material (not shown), the apertures 20 can advantageously extend from the body-facing surface through to one or more layers (not shown) but not completely through to the backside of the laminated liner material (not shown).

Hydrophilic Treatment of Apertures

The entirety of apertures of the present disclosure can be treated with a hydrophilic treatment agent. If not all of the apertures are treated, at least from about 10%, at least from about 25% at least from about 50%, or at least from about 75% of the apertures are treated with a hydrophilic treatment agent that increases the capillary action of the fluid and assures that the liquid flows preferentially through the apertures 20 in the nonwoven liner material 12 and into the absorbent core 16. Additionally, re-wetting is significantly decreased and staining is significantly minimized. Thus, the present disclosure leaves the consumer with a product that feels more dry and clean for an overall improved performing product.

Fluids having viscoelastic properties, such as menses, mucous, blood products, feces, and other body fluids for which personal care products are used have a tendency to interfere with the absorption and distribution properties of the personal care products. Thus, the treated apertures 20 of the present disclosure provide an advantage not only in drawing the fluids through capillary action but also in reducing the viscosity and elasticity of viscoelastic fluids, thus enabling the fluid to flow more easily through the liner material 12 into the absorbent core 16. Additionally, the fouling effects of the fluids are also reduced due to reduced viscosity and or elasticity, particularly of menses fluid.

The hydrophilic treatment agents described herein can exert various combinations of effects on viscosity, elasticity, and fouling, depending on the concentration and deposition rate at which they are applied to the substrate. The hydrophilic treatment agent of the present disclosure can be selected from the group consisting of polyethylene glycol laurates, polyethylene glycol lauryl ethers, and combinations thereof. Advantageously, the polyethylene glycol laurates and polyethylene glycol lauryl ethers are capable of reducing both the viscosity and elasticity of viscoelastic fluid. Examples of suitable polyethylene glycol laurates include, but are not limited to, polyethylene glycol 400 monolaurate, polyethylene glycol 600 monolaurate, polyethylene glycol 1000 monolaurate, polyethylene glycol 4000 monolaurate, polyethylene glycol 600 dilaurate, and combinations thereof. Examples of suitable polyethylene glycol lauryl ethers include, but are not limited to, polyethylene glycol 600 lauryl ether. Notably, the polyethylene glycol lauryl ether and/or polyethylene glycol laurate serves not only as a hydrophilic treatment agent, but is further capable of reducing the fouling properties of viscoelastic fluid. Such hydrophilic treatment agents include, but are not limited to, polyethylene glycol (PEG) 600 lauryl ether and related compounds, polyethylene glycol (PEG) 600 monolaurate and related compounds, and combinations thereof.

In addition to the PEG laurates and PEG lauryl ethers, other polyethylene glycol derivatives can be viscoelastic agents (i.e., are capable of reducing the viscosity and elasticity of viscoelastic fluids) and can be used as hydrophilic treatment agents for the personal care products described herein. As used herein, the term "polyethylene glycol derivative" includes any compound including a polyethylene glycol moiety. Examples of other suitable PEG derivatives include, but are not limited to, PEG monostearates such as PEG 200 monostearates and PEG 4000 monostearate; PEG dioleates such as PEG 600 dioleate and PEG 1540 dioleate; PEG monooleates such as PEG 600 monooleate and PEG 1540 monooleate; PEG monoisostearates such as PEG 200 monoisostearate; and PEG 16 octyl phenyl. Particular polyethylene glycol derivatives for use as hydrophilic treatment agents are those that improve intake time of viscoelastic fluids as well as reduce viscosity and elasticity. Examples of such include, but are not limited to, PEG derivatives including PEG 1540 dioleate, PEG 600 monooleate, PEG 1540 monooleate, and PEG 16 octyl phenyl. These PEG derivatives can be used alone or in combination with PEG 600 monolaurate, PEG 600 lauryl ether, and/or other viscoelastic agents as a hydrophilic treatment agent.

In certain aspects, the hydrophilic treatment agents described herein, such as polyethylene glycol 600 lauryl ether and/or the polyethylene glycol 600 monolaurate, can be used in combination with each other or in combination with other viscoelastant agents. Examples of additional viscoelastant agents that can be used in combination with the hydrophilic treatment agents include, but are not limited to, sodium citrate, dextran, cysteine, Glucopon 220UP (available as a 60% (by weight) solution of alkyl polyglycoside in water from Henkel Corporation), Glucopon 425, Glucopon 600, Glucopon 625. Other suitable viscoelastant agents are described in U.S. Pat. No. 6,060,636. Surprisingly, it has been discovered that certain viscoelastant agents that actually increase the fouling effect of viscoelastic fluids when used alone, will in fact improve fouling effects when used in combination with PEG 600 lauryl ether and/or PEG 600 monolaurate. For example, in one aspect, sodium citrate can be used in combination with PEG 600 monolaurate as a hydrophilic treatment agent. When two or more hydrophilic treatment agents are used in combination, the proportion of each hydrophilic treatment agent applied to the personal care product is preferably in a ratio of from about 1:2 to about 2:1, and more preferably is about 1:1.

The hydrophilic treatment agent can be applied in varying amounts depending on the desired results and application. Typically, the hydrophilic treatment agent is applied to the apertures in an amount of from about 0.1% to about 40%, from about 0.1% to about 20%, or from about 3% to about 12%, by weight of the treated substrate.

In addition to the amount of hydrophilic treatment agent used within the apertures 20, the size of the apertures, the distance from each other on the substrate, and the density of the apertures and/or percent open area play a significant role in contributing to the advantages of the present disclosure. For example, apertures that are too large, (while advantageous in allowing fluid to more easily enter the absorbent system) can be disadvantageous in contributing to increased rewet during product use such as when the wearer applies pressure to the product, for example in a sitting position. On the other hand, very small apertures in combination with low aperture density (low percentage open area), while advantageous for minimizing rewet, can be disadvantageous for fast fluid intake. For menses in particular, this can result in higher accumulation of debris and particulate matter on the liner material. This can lead to the plugging of apertures resulting in a wetter, unclean product. Hydrophilic treatment agents, such as (PEG) 600 lauryl ether, applied into the apertures 20 help to break down the menses by reducing its viscosity and elasticity, improving intake, and reducing debris accumulation on the liner material surface. Research found that about 1 wt. % to about 10 wt. % of such treatments applied in the apertures having a size range of from about 0.1 mm to about 5 mm, from about 0.4 mm to about 1.5 mm, or from about 0.5 mm to about 1.0 mm, along with an aperture density range of about $7.8 \times 10^3$ apertures/$m^2$ to about $1.9 \times 10^6$ apertures/$m^2$, from about $4.7 \times 10^4$ apertures/$m^2$ to about $9.3 \times 10^5$ apertures/$m^2$, or from about $1.6 \times 10^5$ apertures/$m^2$ to about $3.1 \times 10^5$ apertures/$m^2$, in a hydrophobic coated liner material 12 helps to provide the desired balance of fluid intake, reduced debris accumulation, and rewet for improved pad cleanliness and user experience.

Hydrophobic/Hydrophilic Treatments for One-Way Valve

The present disclosure strategically combines hydrophilic and hydrophobic compositions to treat a nonwoven liner material 12 to significantly reduce re-wetting and staining that often occurs during the use of personal care products such as disposable absorbent articles 10. The aperture treated liner material 12 functions as a 'one-way valve' that allows fluid to more easily migrate from the body-facing surface to the absorbent core 16. Due to the design and composition used in the present disclosure, there is less undesirable re-wetting or flowback caused by the fluid re-entering from the absorbent core 16 to the body-facing surface of the liner material 12. One way to achieve such a 'one-way valve' in the nonwoven liner material 12 of the present disclosure is by aperture design, such as a conical aperture design with a wider diameter aperture on the body-facing side of the liner material 12 than on the opposing back side of the liner material 12 in combination with strategic hydrophilic and hydrophobic treatments. The aperture 20 is treated with a hydrophilic treatment agent while either or both the body-facing surface of the liner material 12 and the back side of the liner material 12 are treated with a hydrophobic or a superhydrophobic composition. Use of a 'one way valve' system drives the fluid into the absorbent layer 16, away from the wearer's body such that the wearer feels drier and cleaner for an overall improved performing product.

EXAMPLES

The following examples further describe and demonstrate aspects within the scope of the present disclosure. The examples are given solely for the purpose of illustration and are not to be construed as limitations of the present disclosure, as many variations thereof are possible without departing from the spirit and scope of the disclosure.

As illustrated by way of the following examples with no intended limitations, the 3-D materials of the present disclosure are nonwovens with different 3-D topography exemplified by bumps, channels, corrugations, grooves, valleys, dots and the like of varying heights, depths, dimensions, and spacing. The hydrophobic treatment can be a hydrophobic polymer that is dispersible in water including, but not limited to, fluorinated or perfluorinated polymers, though non-fluorinated treatments are preferred. Likewise, hydrophilic treatments can be various surfactants. The hydrophilic treatment agent is preferably selected from the group consisting of polyethylene glycol laurates, polyethylene glycol lauryl ethers, and combinations thereof.

Example 1

In Example 1, 10 cc of real breastfed baby feces/BM was applied to a diaper construction including a surge and an absorbent core disposed between a fluid permeable bodyside liner (BSL) and a fluid-impermeable outercover to measure BM absorption. The BM was applied using a BM gun and the absorption test conducted using the BM Plate Test Method. The liner was a 5" by 14" rectangular piece of a 60 gsm 3-D textured Coform with bumps and valleys between the bumps (see FIG. 3), including about 60% CF405 pulp and 40% VMX2330 VISTAMAXX brand polymer available from Exxon Mobile Chemical Company. The liner was neither apertured nor treated with any composition to improve BM absorption. The surge material was a 50 gsm bonded carded web including 2.25 denier rayon fibers and was apertured with approximately 2.0 mm diameter and about 13 apertures per square inch density. The absorbent core included about 70% superabsorbent material (SAM) and was wrapped with a 10 gsm Spunbond-meltblown-spunbond (SMS) nonwoven core wrap. Prior to diaper construction, 5 each of liner and surge materials were weighed to get an average dry weight. Similarly, the diaper, absorbent core, and outercover weights and diaper thickness (caliper) were measured and recorded prior to insult. The four corners of the BM plate were then adjusted to match diaper thickness and checked to make sure the plate was level. The diaper was placed between the lower and upper plates and insulted with BM. The diaper was left in the test apparatus for 2 minutes after insult, and then placed on a vacuum box to measure the amount of BM pooling on the liner. Four paper towels were placed on top of the diaper and the diaper flipped with the paper towels down on top of the vacuum box and covered with a silicone sheet to seal the vacuum. The vacuum box was turned on pulling a pressure of 5 inches of water for 1 minute. In addition to the BM picked-up by paper towels on the vacuum box, the excess BM left on the BM plate was removed using an additional paper towel. The BM amount picked-up by the paper towels from the vacuum box along with the excess BM left on the plate was recorded as the total pooled BM. To determine BM amount in each diaper layer, liner and surge pieces were weighed individually while the core wrap, absorbent core, and outer cover were weighed together as "core." The initial dry weights of each layer were then subtracted from the final weights and the percent BM in each layer determined by dividing the weight of BM in each layer by the total amount of BM insult.

Three (N=3) samples were tested for each of the examples. The amounts of BM in each layer in the 3 samples were then averaged to get BM pooled on the liner, in the liner, in the surge, and in the core. Results in FIG. 1 (code 1) show that in this Example 1, the amount of BM pooling on the liner was about 60%, about 37% in the liner, and less than 2% in both the surge and the core.

Example 2

Example 2 is the same as Example 1 except that the 3-D coform bodyside liner had approximately 2 mm diameter apertures in the valley areas between the 3-D bumps to provide a fluid pathway to the core. FIG. 1 (code 2) results for Example 2 show that BM pooling was reduced from about 60% to about 47% and transfer to core increased from less than 2% to about 9% compared to Example 1.

Example 3

Example 3 is the same as Example 2 except that the coform BSL material was treated on the 3-D bumps with a 5% add-on hydrophobic treatment, OLEOPHOBOL® CP-X, a dispersion of perfluorinated acrylic copolymer available from Huntsman, and in the valley areas between the bumps with a 5% add-on hydrophilic, Lutensol A65N, nonionic surfactant treatment available from BASF. The diaper construction did not have a surge layer. FIG. 1 (code 3) results show a higher BM transfer to the core (25%) compared to Example 1 (less than 2%) and about 9% in Example 2. Surprisingly, the amount of BM pooled on the liner was slightly higher than in Example 2, perhaps as a result of reduced void space due to the missing surge.

Example 4

Example 4 diaper construction had no surge similar to Example 3 except that the bodyside liner was a hydroentangled 3-D material available from Textor Technologies Pty Ltd, 41 Tullamarine Park Road, VIC 3043, Melbourne, Australia. The 3-D Textor material includes micro-perforations or apertures between the bumps. The BM amount in the core (22%) is comparable to Example 3 at 25%. However, the BM pooled at 39% is substantially lower than for Examples 1, 2, and 3.

Cleaner-Looking Diaper Visual Perception after BM Insult for Examples 1-4

Figure 8:
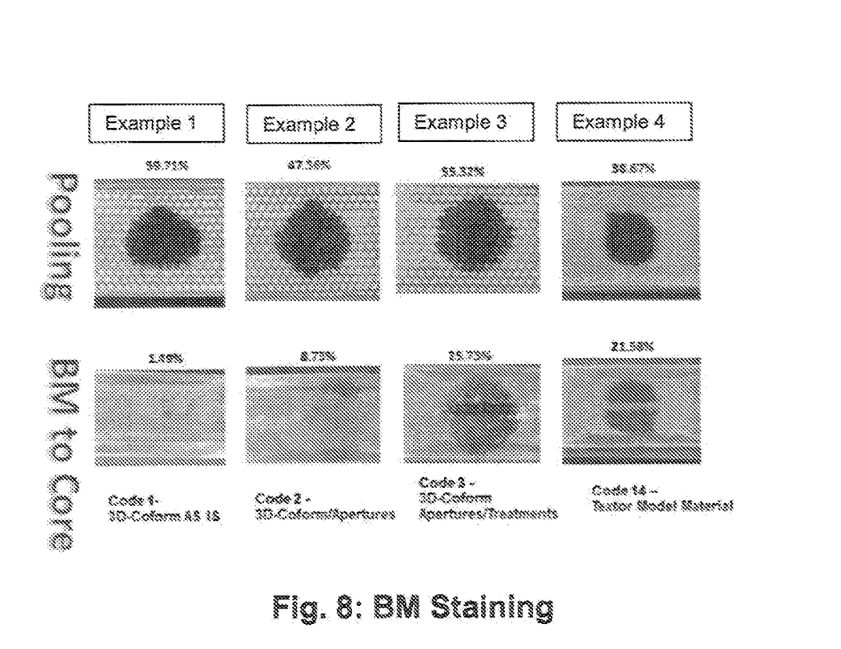
FIG. 8 is a photographic representation of the results obtained in Examples 1-4 with respect to BM staining.
Figure 9:
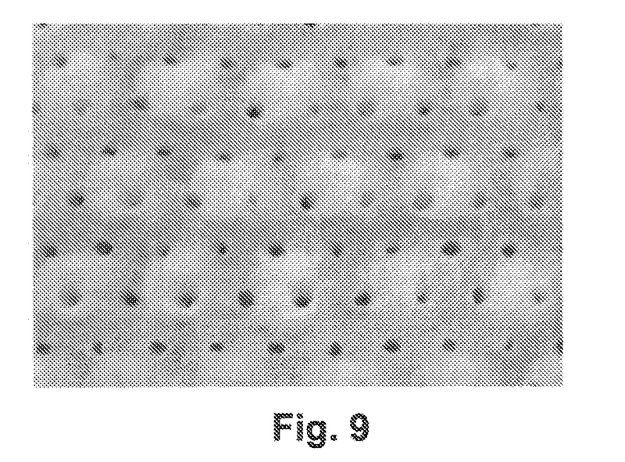
FIG. 9 is a photographic illustration of the 3-D coform liner material pin apertured to a 12 gsm spunbond and used as code 8 in Example 5.
Figure 10:
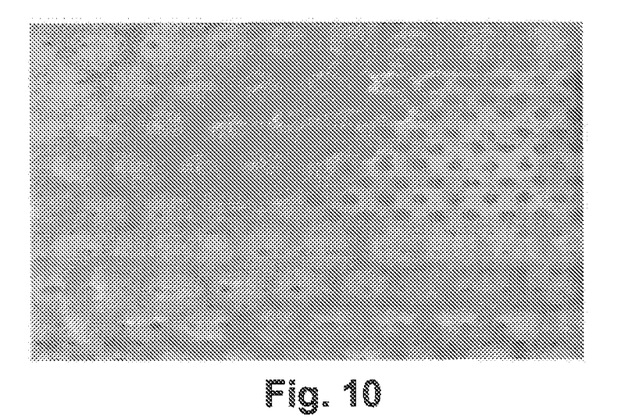
FIG. 10 is a photographic illustration of the 3-D coform liner material pin apertured to a 12 gsm spunbond, with a treated and apertured target area, used as code 13 in Example 6.
Figure 11:
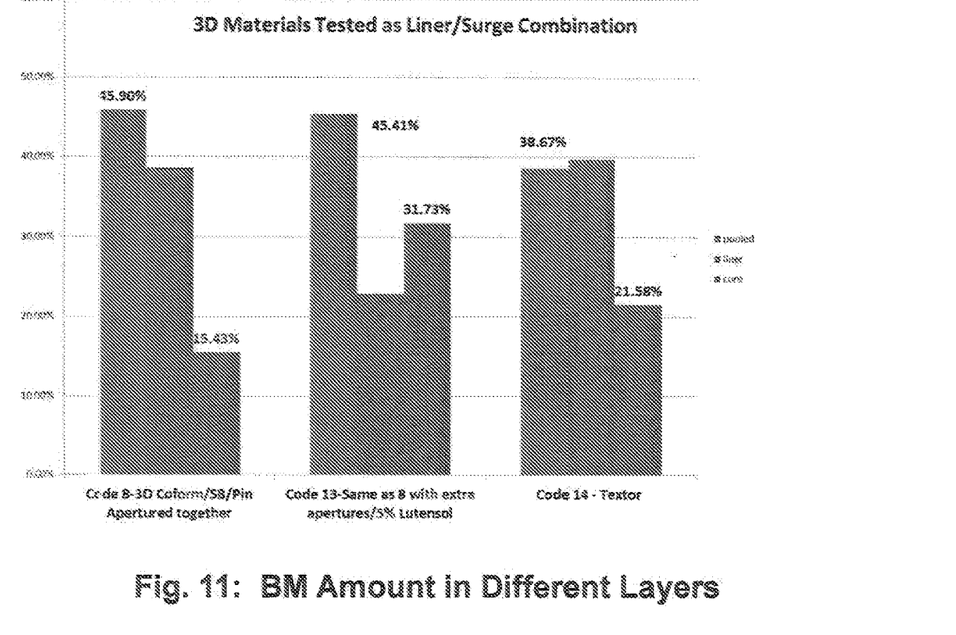
FIG. 11 is a graphical representation of the results obtained in Examples 4-6 with respect to BM amount in different layers.
Figure 12:
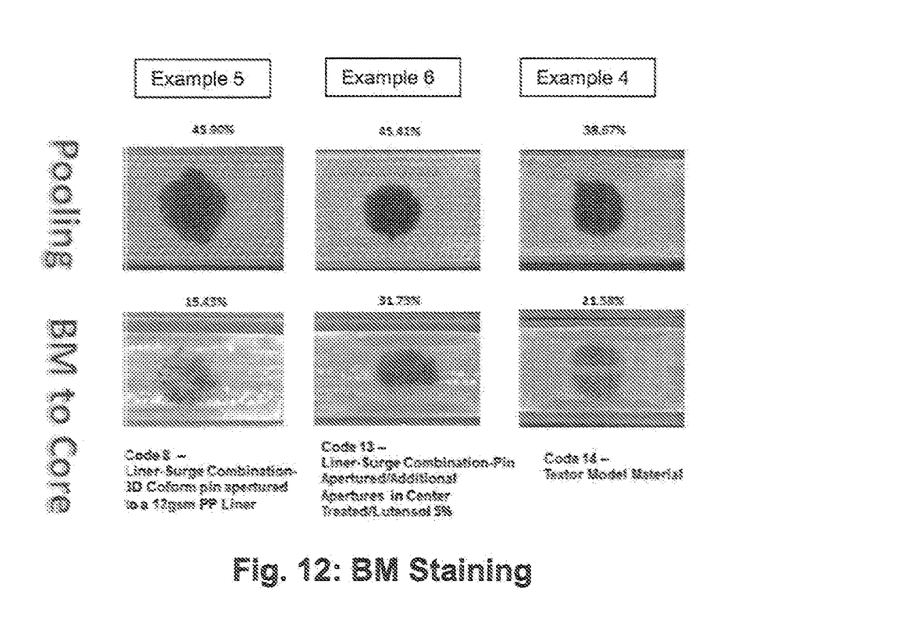
FIG. 12 is a photographic representation of the results obtained in Examples 4-6 with respect to BM staining.

A diaper soiled with BM is not clean. However, a diaper that effectively manages BM looks relatively clean compared to one that does not, giving the caregiver a more positive perception about the product. FIG. 8 shows BM pooling on the liner for Examples 1 through 4. It can be seen that apertures and treatment in Example 3 dewater BM around the edges that could provide a perception of a cleaner-looking surface and a cue that the product is functional. A combination of cleaner-looking diaper and a smaller stain-size is desirable.

Example 5

Figure 3:
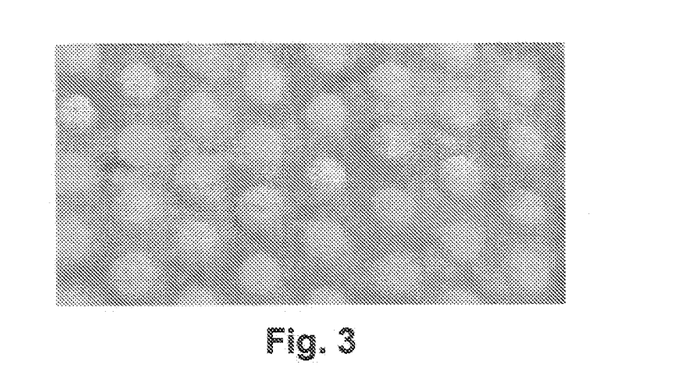
FIG. 3 is a photographic illustration of the liner material used as code 1 in Example 1.
Figure 4:
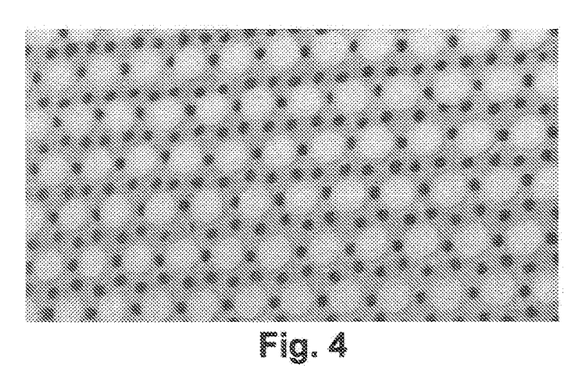
FIG. 4 is a photographic illustration of the liner material with apertures used as code 2 in Example 2.
Figure 5:
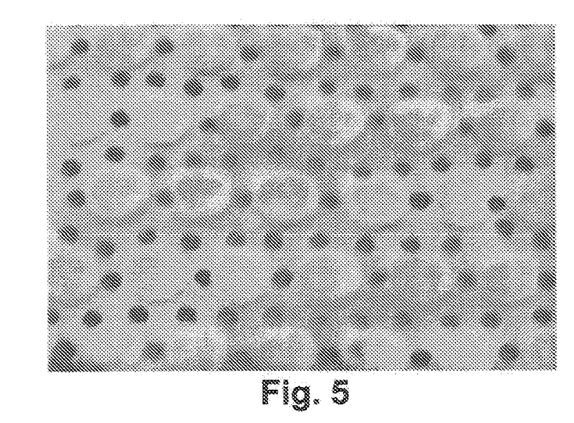
FIG. 5 is a photographic illustration of the liner material with apertures and treatments used as code 3 in Example 3.
Figure 6:
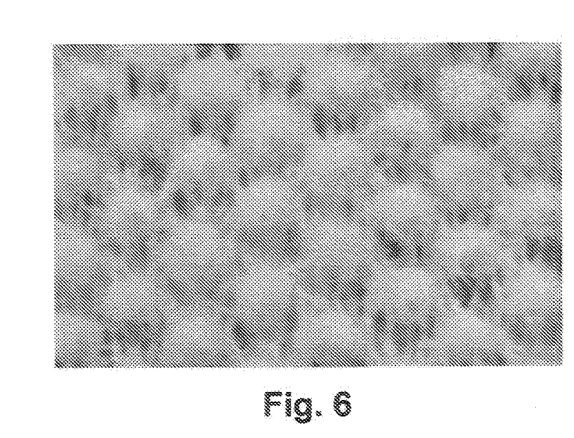
FIG. 6 is a photographic illustration of the Textor liner material used as code 14 in Example 4.
Figure 7:
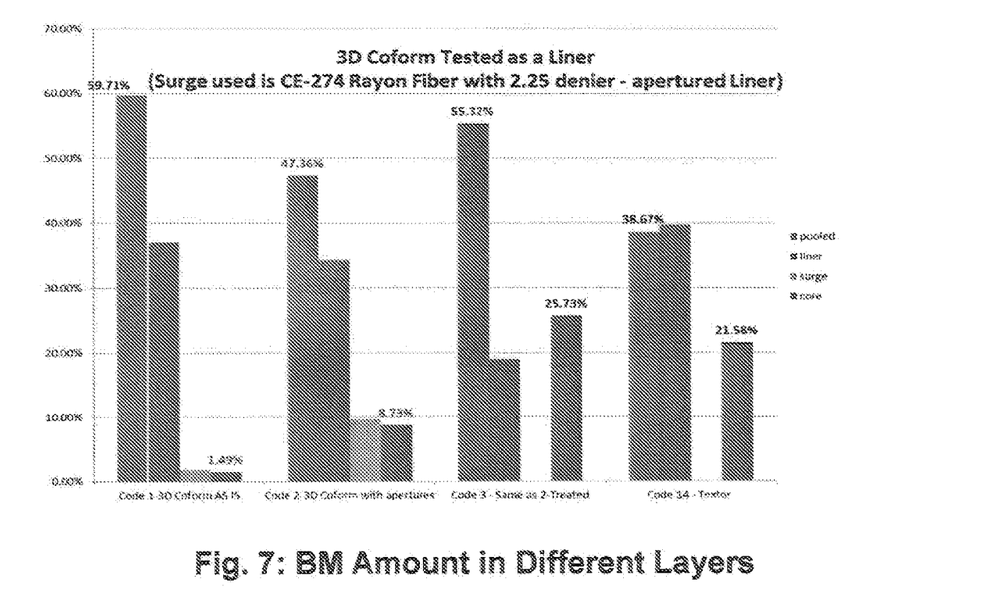
FIG. 7 is a graphical representation of the results obtained in Examples 1-4 with respect to BM amount in different layers.

Example 5 is a 5" by 14" rectangle of a 60 gsm 3-D textured coform with bumps (60/40) pulp/vistamaxx polymer VMX2330 produced on a K-C pilot line. The 3-D Coform material was pin apertured with approximately 1 mm diameter heated pins to a 12 gsm Polypropylene Spunbond treated with SF19 surfactant to test a liner/surge combination concept within the diaper construction using the same test protocol as Example 1. FIG. 3 (code 8) results show 45% BM pooling on the liner and 15% in the core.

Example 6

Example 6 is the same as Example 5 except that additional apertures of approximately 2 mm in diameter were provided in the insult target zone and the material was treated with a Lutensol® hydrophilic treatment at approximately 5% add-on based on sample weight. FIG. 3 (code 13) shows a relatively low BM pooling (45%) on the liner but with a much higher BM amount (31%) transferred to the core.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Disclosure are, in relevant part, incorporated herein by reference; the citation of any document is not to be construed as an admission that it is prior art with respect to the present disclosure. To the extent that any meaning or definition of a term in this written document conflicts with any meaning or definition of the term in a document incorporated by reference, the meaning or definition assigned to the term in this written document shall govern.

While particular aspects of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A bodyside liner material for use in disposable absorbent personal care products, the liner material having a projection layer and comprising:
   a plurality of raised areas extending in a z-direction from the projection layer;
   a plurality of apertures through the liner material;
   a hydrophobic treatment agent disposed on the raised areas, wherein the hydrophobic treatment agent is a superhydrophobic composition;
   a plurality of land areas disposed between the raised areas; and
   a hydrophilic treatment agent disposed either within the land areas or adjacent the apertures, wherein the liner material in the land areas is hydrophilic prior to the disposition of the hydrophilic treatment agent.

2. The liner material of claim 1, wherein the hydrophilic treatment agent is a surfactant.

3. The liner material of claim 2, wherein the surfactant is nonionic.

4. The liner material of claim 1, wherein the hydrophilic treatment agent further comprises a viscoelastant agent selected from the group consisting of sodium citrate, dextran, cysteine, glucopan, and combinations thereof.

5. The liner material of claim 1, wherein the hydrophilic treatment agent is selected from the group consisting of polyethylene glycol laurates, polyethylene glycol lauryl ethers, and combinations thereof.

6. The liner material of claim 1, wherein the land areas are depressed areas alternating with the plurality of raised areas, wherein the depressed areas extend into the projection layer.

7. The liner material of claim 1, wherein the apertures are disposed only in the land areas.

8. The liner material of claim 1, wherein the apertures are spaced regardless of raised and land areas.

9. The liner material of claim 1, wherein the liner material when untreated is hydrophobic.

10. A bodyside liner material for use in disposable absorbent personal care products, the liner material having a projection layer and comprising:

a plurality of raised areas extending in a z-direction from the projection layer;

a plurality of depressed areas alternating with the plurality of raised areas, wherein the depressed areas extend into the projection layer, and wherein the depressed areas are hydrophilic;

a plurality of apertures through the liner material, wherein the apertures are disposed only in the depressions;

a hydrophobic treatment agent disposed on the raised areas, wherein the hydrophobic treatment agent is a superhydrophobic composition; and a hydrophilic treatment agent disposed either within the depressed areas or adjacent the apertures, wherein the liner material in the land areas is hydrophilic prior to the disposition of the hydrophilic treatment agent.

11. The liner material of claim 10, wherein the raised areas have a height measured from the projection layer, wherein the depressed areas have an average depth measured into the projection layer, and wherein the height is greater than the average depth.

12. A personal care article comprising a nonwoven fluid permeable liner material having a body-facing surface and an opposing backside surface, a fluid impermeable backsheet and at least one intermediate layer disposed therebetween, wherein the fluid permeable liner material comprises raised areas and apertures, wherein at least some of the raised areas are treated with a hydrophobic treatment agent, wherein the hydrophobic treatment agent is a superhydrophobic composition, wherein at least some of the apertures are treated with a hydrophilic treatment agent, and wherein the liner material in the apertures is hydrophilic prior to the disposition of the hydrophilic treatment agent.

* * * * *